(12) United States Patent
Gabl et al.

(10) Patent No.: US 8,569,864 B2
(45) Date of Patent: Oct. 29, 2013

(54) PIEZO-ACOUSTIC THIN FILM RESONATOR HAVING A CRYSTALLINE ZINC OXIDE LAYER

(75) Inventors: Reinhard Gabl, St. Peter im Sulmtal (AT); Mathias Link, München (DE)

(73) Assignee: Siemens Aktiengesellschaft, Munich (DE)

( * ) Notice: Subject to any disclaimer, the term of this patent is extended or adjusted under 35 U.S.C. 154(b) by 1142 days.

(21) Appl. No.: 11/663,831

(22) PCT Filed: Aug. 2, 2005

(86) PCT No.: PCT/EP2005/053753
§ 371 (c)(1),
(2), (4) Date: Sep. 9, 2008

(87) PCT Pub. No.: WO2006/034906
PCT Pub. Date: Apr. 6, 2006

(65) Prior Publication Data
US 2009/0079442 A1   Mar. 26, 2009

(30) Foreign Application Priority Data
Sep. 28, 2004  (DE) .......................... 10 2004 047 023

(51) Int. Cl.
*H01L 29/04* (2006.01)
*H03H 9/00* (2006.01)
(52) U.S. Cl.
USPC .................... 257/532; 333/187; 257/E29.001
(58) Field of Classification Search
USPC ............................ 257/532, E29.001; 333/187
See application file for complete search history.

(56) References Cited

U.S. PATENT DOCUMENTS

| 5,126,921 A * | 6/1992 | Fujishima et al. ............ 361/525 |
| 6,515,558 B1 * | 2/2003 | Ylilammi ....................... 333/189 |
| 7,657,983 B2 * | 2/2010 | Aigner et al. ................ 29/25.35 |
| 2010/0107389 A1 * | 5/2010 | Nessler et al. ............... 29/25.35 |

FOREIGN PATENT DOCUMENTS

| EP | 1 124 328 A1 | 8/2001 |
| WO | 2004/017063 | 2/2004 |
| WO | WO 2004/017063 A2 | 2/2004 |

OTHER PUBLICATIONS

"Improvement of crystallinity of ZnO thin film and electrical characteristics of film bulk acoustic wave resonator by using Pt buffer layer," Yamada et al., Vacuum Elsevier UK, vol. 74, No. 3-4, Jun. 7, 2004, pp. 689-692, XP002352544.
"Sputtered X-Axis Inclined Piezoelectric Films and Shear Wave Resonators," Wang et al., Proceedings of the Annual Frequency Control Symposium, Jun. 1-3, 1983, vol. Symp. 37, XP000647259.

(Continued)

*Primary Examiner* — Colleen Matthews
(74) *Attorney, Agent, or Firm* — King & Spalding L.L.P.

(57) ABSTRACT

A capacitor structure includes a lower electrode layer disposed on a substrate, an upper electrode layer and a crystalline zinc oxide-containing dielectric layer interposed between the electrode layers. The amorphous dielectric intermediate layer is interposed between the lower electrode layer and the crystalline zinc oxide-containing dielectric layer. A method for producing the aforementioned capacitor structure is also disclosed. The amorphous dielectric layer is adapted to produce during deposition of the zinc oxide an electrical field which is tipped in relation to the normal to the surface of the substrate surface or the lower electrode layer. The zinc oxide monocrystals grow at an angle, thereby providing a crystalline dielectric layer that can be induced to shear vibrations.

19 Claims, 2 Drawing Sheets

(56) References Cited

OTHER PUBLICATIONS

"Transmission electron microscopy study of interface microstructure in ZnO thin films grown on various substrates," Yoshino et al., Materials Research Society Symposium Proceedings, Dec. 2, 1996, vol. 441, XP008055125.

"First results on label-free detection of DNA and protein molecules using a novel integrated sensor technology based on gravimetric detection principles," Gabl et al., Biosensors & Bioelectronics, Elsevier Science Publishers, vol. 19, No. 6, Sep. 11, 2003, XP002320316.

Yamada et al., "Improvement of crystallinity of ZnO thin film and electrical characteristics of film bulk acoustic wave resonator by using Pt buffer layer", Vacuum Elsevier UK, vol. 74, No. 3-4, Jun. 7, 2004, pp. 689-692, XP-002352544.

Wang et al., "Sputtered C-Axis Inclined Piezoelectric Films and Shear Wave Resonators", Proceedings of the Annual Frequency Control Symposium, Jun. 1-3, 1983, vol. 37, pp. 144-150, XP-000647259.

Yoshino et al., "Transmission electron microscopy study of interface microstructure in ZnO thin films grown on various substrates", Materials Research Society Symposium Proceedings, Dec. 2, 1996, vol. 441, pp. 241-246, XP008055125.

Gabl et al., "First results on label-free detection of DNA and protein molecules using a novel integrated sensor technology based on gravimetric detection principles", Biosensors & Bioelectronics, Elsevier Science Publishers, vol. 19, No. 6, Sep. 11, 2003, pp. 615-620, XP-002320316.

\* cited by examiner

- Provide a substrate
- Produce a lower electrode layer on the substrate
- Produce the amorphous dielectric layer
- Produce the zinc oxide layer
- Produce the upper electrode layer

PIEZO-ACOUSTIC THIN FILM RESONATOR HAVING A CRYSTALLINE ZINC OXIDE LAYER

BACKGROUND OF THE INVENTION

1. Field of the Invention

The invention relates to a capacitor structure comprising a lower electrode layer disposed on a substrate and an upper electrode layer and a crystalline zinc oxide-containing dielectric layer interposed between the electrode layers. In addition a method for producing the capacitor structure and a use of the capacitor structure are specified.

2. Description of the Related Art

A capacitor structure having the described layer set-up is known from WO 2004/017063 A2 for instance. The capacitor structure (thin film capacitor) forms a piezo-acoustic thin film resonator (Film Bulk Acoustic Resonator, FBAR). The crystalline dielectric layer is a polycrystalline layer made of zinc oxide (ZnO). This layer forms a piezo-electric layer of the resonator. The electrode layers are made of platinum for instance. The electrode layers and the piezoelectric layer are arranged next to one another such that an electrical control of the electrode layers with an electrical alternating field results in the resonator vibrating at a resonance frequency. The resonance frequency of the vibration depends on the layer thickness of the layers of the capacitor structure. Which vibration mode (longitudinal vibration or sheer vibration) is induced depends on a crystal structure of the zinc oxide monocrystal and on a relative alignment of the zinc oxide monocrystal to the disposed electrical alternating field.

A vapor deposition method is carried out in order to produce the layers of the capacitor structure on a substrate, for instance a silicon substrate. In this process, the lower electrode layer, made of polycrystalline platinum for instance, is first deposited onto the silicon substrate. Zinc oxide is deposited onto the lower electrode layer made of platinum. Zinc oxide monocrystals grow at an (002)-orientation without additional measures. This means that the polar c-axis of the zinc oxide is oriented perpendicular to the substrate surface and/or to the electrode surface. This allows the resulting resonator to be optimally induced to longitudinal vibrations.

The known resonator is used to detect a substance of a fluid. To this end, the fluid is passed through to a surface segment of the resonator, with the substance to be detected being sorbed on the surface segment. The sorption leads to a change in the mass of the resonator results and thus to a change in the resonance frequency of the resonator.

If a fluid in the form of a liquid is to be examined, and the resonance frequency of the resonator is to be determined whilst the fluid is passed through, it is particularly advantageous to be able to induce the known resonator to sheer vibrations. Sheer vibrations are almost not attenuated by means of the fluid, thereby resulting in a relatively high quality resonator in comparison with the longitudinal vibrations and thus in a relatively high detectability for the substance of the fluid. The described production method results in an (002) orientation of the zinc oxide monocrystal. To achieve a resonator which can be induced to sheer vibrations, the zinc oxide monocrystals must grow at an angle. WO 2004/017063 A2 does not discuss how this can be achieved.

SUMMARY OF THE INVENTION

The object of the present invention is to indicate how a capacitor structure is achieved for a thin film resonator, which can be induced to sheer vibrations.

To achieve the object, a capacitor structure comprising a lower electrode layer disposed on a substrate, an upper electrode layer and crystalline zinc oxide-containing dielectric layer interposed between the electrode layers is specified. The capacitor structure is characterized in that an amorphous dielectric intermediate layer is interposed between the lower electrode layer and the crystalline zinc oxide-containing dielectric layer.

To achieve the object, a method for producing the capacitor structure according to one of the preceding claims is specified, having the method steps: a) providing the substrate, b) producing the lower electrode layer on a substrate surface of the substrate, c) producing the amorphous intermediate layer on the lower electrode layer, d) producing the crystalline zinc oxide-containing dielectric layer on the intermediate layer, and e) producing the upper electrode layer on the crystalline zinc oxide-containing dielectric layer.

In accordance with a further aspect of the invention, a use of the capacitor structure as a piezo-acoustic resonator is specified. In this way, the crystalline zinc oxide-containing dielectric layer forms a piezo-electric layer of the resonator. The piezo-electric layer and the electrode layers are arranged next to one another such that an electrical control of the electrode layers results in the resonator vibrating at a specific resonance frequency.

A deposition from a vapor phase is preferably carried out in order to produce the lower electrode layer, the amorphous intermediate layer, the crystalline zinc oxide-containing dielectric layer and/or the above electrode layer. The deposition from the vapor phase can comprise a physical vapor deposition (PVD) or a chemical vapor deposition (CVD). A method of this type is a reactive sputtering for instance, with which the zinc oxide film is deposited.

In accordance with the present invention, an amorphous intermediate layer is deposited on the lower electrode layer, which consists of platinum for instance. This intermediate layer enables an electrical field to be produced during the production of the dielectric zinc oxide-containing layer such that lateral field components appear on the substrate surface and/or on the lower electrode layer. Zinc oxide is deposited on the lower electrode layer at an angle as a result of the lateral field components. In a particular embodiment of the method, a deposition of zinc oxide from the vapor phase is thus carried out in order to produce the crystalline dielectric layer and an electrical field is produced during the deposition of the zinc oxide, said electrical field comprising lateral field components in respect of the substrate surface of the substrate. Field components would only appear without the dielectric intermediate layer by electrically controlling the lower electrodes during the deposition, said field components being essentially oriented perpendicular to the substrate surface.

No epitaxial growth of the zinc oxide monocrystal is additionally carried out as a result of the intermediate layer being amorphous. The preferential direction of the growth of the zinc oxide monocrystal is not predetermined. The tipping of the growing zinc oxide monocrystals can thus be adjusted in any manner.

The amorphous intermediate layer allows a tipping of the polar crystal axis of the zinc axis to be available. Thus, with a tipping of 40° or 90°, the resonator can be induced to pure sheer vibrations. Nevertheless, with a lesser dropping tipping, for instance with a tipping of 16°, a resonator results which can be induced to sheer vibrations and which comprises a sufficiently high detectivity also in the presence of a fluid to be examined.

Any type of inorganic or organic material is conceivable as a material of the intermediate layer. In a particular embodiment, the intermediate layer comprises at least one ceramic material selected from the aluminum oxide ($Al_2O_3$), silicon dioxide ($SiO_2$), titanium dioxide ($TiO_2$) and/or zirconium dioxide ($ZrO_2$) group. Aluminum oxide has proven particularly advantageous.

In a particular embodiment, the intermediate layer comprises an intermediate layer thickness selected from the range of exclusively 20 nm to exclusively 500 nm. In particular, the intermediate layer thickness is selected from the range of 50 nm to 200 nm. These intermediate layer thicknesses are sufficient to achieve a tipping of the zinc oxide monocrystals. At the same time, a capacitor structure is available, which has a sufficiently high mass sensitivity as a piezo-acoustic resonator.

In a particular embodiment, the crystalline zinc oxide-containing dielectric layer comprises a layer thickness which is selected from the range of exclusively 0.1 μm to exclusively 20 μm. The resonance frequency of the vibration of the resonator realized with the capacitor structure is preferably selected from the range of exclusively 500 MHz to exclusively 10 GHz. These measures result in a particularly high mass sensitivity compared with the substance.

Any electrode material is conceivable as an electrode material of the lower electrode layer. In a particular embodiment, the lower electrode layer comprises an electrode material selected from the wolfram and/or platinum group. These electrode materials have proven themselves with the use of semiconductor substrates.

Any type of electrode material is likewise conceivable as an electrode material of the above electrode layer. It is particularly advantageous to select the electrode material of the above electrode from the aluminum and/or gold group. In particular, the use of gold enables the upper electrode layer to be used as a chemically sensitive coating for sorbing the substance of the fluid. By way of example, the substance has sulfur atoms. Sulfur-gold bonds can herewith be formed, so that the substance is sorbed.

Any substrate is conceivable as a substrate (carrier element of the capacitor structure). The substrate is preferably a semiconductor substrate with a semiconductor material. In particular, the semiconductor material is selected from the silicon and/or gallium arsenide group. In this way, the substrate can be monocrystalline or polycrystalline. The said semiconductor materials are suited to use in bipolar and CMOS (Complementary Metal Oxide Semiconductor) technology for integrating control and/or evaluation facilities of the resonator.

At least one facility for the acoustic insulation of the capacitor structure and of the substrate is preferably available. The capacitor structure and/or the resonator and the substrate are acoustically insulated from one another. The acoustic insulation ensures that the resonance frequency of the resonator is independent of the substrate. A relatively high mass sensitivity results. The facility for the acoustic insulation is a Bragg reflector for instance, which consists of λ/4 thick layers of different acoustic impedance. Alternatively to this, the facility is formed by means of a cavity in the substrate.

The capacitor structure is used in particular to detect a substance of a fluid. The fluid can be gaseous. The fluid is preferably a liquid. The following method steps are carried out for detection purposes: a) combining the fluid and the piezo-acoustic resonator such that the substance can be sorbed on the surface segment of the resonator and b) determining a resonance frequency of the resonator, with the quantity of the substance sorbed on the surface segment being concluded from the resonance frequency. In this way, a surface segment for sorbing a substance of a fluid is arranged on the resonator such that the resonance frequency of the resonator is dependent on a quantity of the substance sorbed on the surface segment. The surface segment can be formed here by the upper electrode layer, for instance an electrode layer made of gold (see above). In particular, the formation of the surface segment is also conceivable by a chemically sensitive coating of the resonator.

The determination of the resonance frequency can be carried out according to a sorption carried out in absence of the fluid. As a resonator is available with the invention, said resonator being able to be induced to sheer vibrations, the determination of the resonance frequency is preferably carried out in the presence of the fluid.

To summarize, the following significant advantages result with the invention:

The additional dielectric amorphous intermediate layer enables lateral field components during the deposition of the zinc oxide layer. The deposition of tipped zinc oxide is hereby possible.

No preferential direction for the growth of the zinc oxide monocrystal is predetermined by the amorphous intermediate layer.

A dielectric layer with tipped zinc oxide is available approximately independently of electrode material of the lower electrode layer. No adjustment of a grid constant and/or of the electrode material needs to be considered for instance with the selection of the electrode material of the lower electrode layer.

An acoustic resonator is available in a simple manner as a result of the zinc oxide film with the tipped zinc oxide monocrystals, said acoustic resonator can be induced to sheer vibrations.

The invention is described in more detail below with reference to a number of exemplary embodiments and the associated figures. The figures are schematic and do not represent any illustrations which are to scale.

BRIEF DESCRIPTION OF THE DRAWING FIGURES

DETAILED DESCRIPTION OF THE INVENTION

Figure 1:
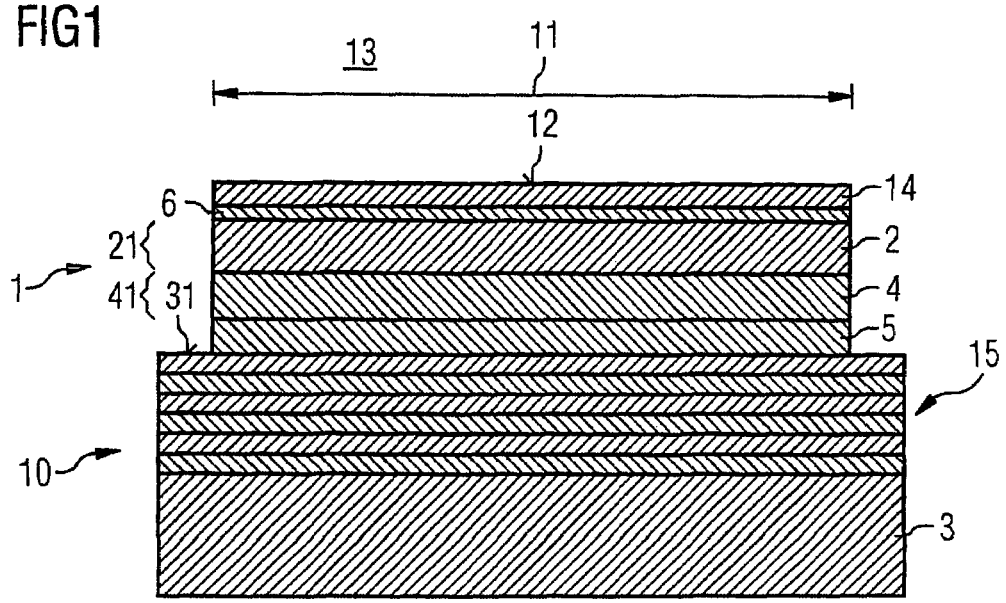
FIG. 1 shows a cross-sectional view from the side of a capacitor structure made of a zinc oxide film on a substrate surface of a substrate

A capacitor structure 1 having a crystalline dielectric layer made of polycrystalline zinc oxide (zinc oxide film) 2 on a semiconductor substrate 3 made of silicon (FIG. 1) is given. The zinc oxide film 2 forms the capacitor structure 1 together with the electrode layers 5 and 6. An amorphous dielectric layer 4 made of aluminum oxide is available between the lower electrode layer 5 and the zinc oxide film 2. The intermediate layer thickness 41 of the intermediate layer 4 amounts to approximately 50 nm.

The capacitor structure 1 is used to detect a substance of a fluid 13. To this end, the capacitor structure 1 is designed to form a piezo-acoustic thin film resonator 10, which is applied to the substrate surface 31 of the semiconductor substrate 3. The layer thickness 21 of the zinc oxide film 2 amounts to approximately 0.8 μm. The lateral extension 11 of the resonator 10 amounts to approximately 100 μm.

The electrode layers 5 and 6 are arranged on two sides of the zinc oxide film 2 which face away from one another. The layer thickness of the lower electrode layer 5 amounts to approximately 0.5 μm. The layer thickness of the upper electrode layer 6 amounts to approximately 0.1 μm. The lower electrode layer 5 is made of platinum. The upper electrode layer 6 is made of gold.

The zinc oxide film 2 consists of a plurality of zinc oxide monocrystals. The zinc oxide monocrystals are tipped against the substrate surface 31 of the semiconductor substrate 3. The resonator 10 formed with the capacitor structure 1 can thus be induced to sheer vibrations in parallel to substrate surface 31.

The resonator 10 has a surface segment 12, on which a substance of a fluid 13 can be sorbed. To this end, the resonator 10 has a chemically sensitive coating 14. The chemically sensitive coating 14 is applied to the electrode 6.

To increase the mass sensitivity of the resonator 10 for a specific substance, the semiconductor substrate 3 and the resonator 10 are acoustically insulated from one another with the aid of a facility for acoustic insulation 15. In accordance with the present example, the facility 15 is a Bragg reflector having λ/4 thick layers of different acoustic impedance.

Figure 2:
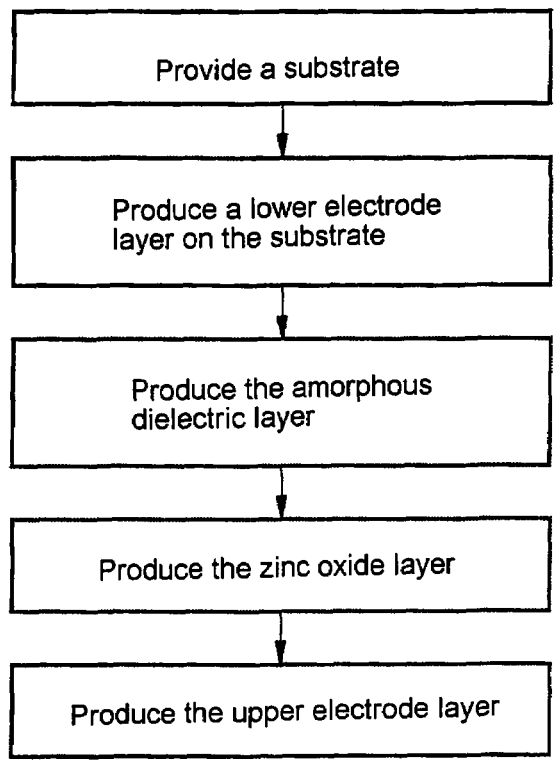
FIG. 2 shows a method for producing the zinc oxide film.

The following method steps are carried out to produce the capacitor structure 1 (FIG. 2): a) providing the substrate, b) producing the lower electrode layer on a substrate surface of the substrate, c) producing the amorphous intermediate layer on the lower electrode layer, d) producing the crystalline zinc oxide-containing dielectric layer on the intermediate layer, and e) producing the upper electrode layer on the crystalline zinc oxide-containing dielectric layer. The production of the individual layers is carried out in each instance by vapor phase deposition. During the deposition of the zinc oxide film 2 an electrical field having field components is produced by electrically controlling the lower electrode layer 5, said field components being aligned laterally to the substrate surface 31. A zinc oxide film 2 having zinc oxide monocrystals, which comprises a preferred orientation results. The preferred orientation is characterized by a tipping of the c-axis of the zinc oxide monocrystals about approximately 16° toward the normal of the surface of the substrate surface 31.

Figure 3:
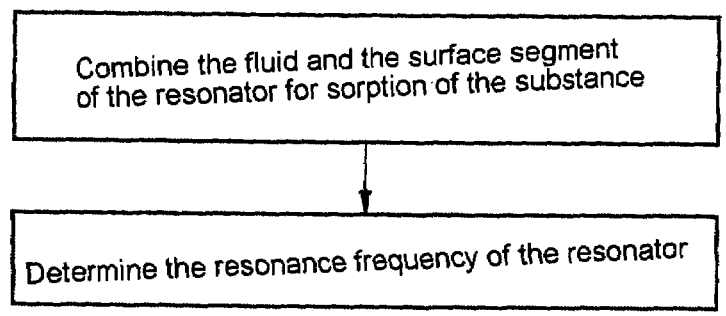
FIG. 3 shows a method for detecting a substance.

The capacitor structure 1 and/or the resonator 10 is used to detect a substance of a fluid 15 in the form of a liquid. The chemically sensitive surface segment 12 of the resonator 10 and the fluid 13 are combined (FIG. 3) in a first step to detect the substance of the fluid 15. The fluid 13 and the resonator 10 are combined such that the substance of the fluid 13 can be sorbed on the surface segment 12 of the resonator 10. The sorption causes the mass of the resonator 10 to change. A subsequent measurement of the resonance frequency of the resonator 10 allows the type of substance and its concentration in the fluid 13 to be concluded. The sorption of the substance changes the resonance frequency of the resonator 10 in comparison with the resonance frequency of the resonator 10, on the surface segment 12 of which no substance is sorbed. To be able to determine the change in the resonance frequency, a resonator 10 with a known resonance frequency is used. In an alternative embodiment, the resonance frequency of the resonator is determined without sorbed substance prior to combining the fluid and the resonator.

The invention claimed is:

1. A capacitor structure (1) for forming a piezo-acoustic resonator, comprising:
    a lower electrode layer (5) arranged on a substrate surface (31) of a substrate (3);
    an upper electrode layer (6);
    a crystalline zinc oxide-containing dielectric layer (2) arranged between the electrode layer (5, 6), which has a plurality of zinc oxide single crystals each with a polar crystal axis, the polar crystal axes of the zinc oxide single crystals of the dielectric layer being tipped relative to the substrate surface (31); and
    an amorphous dielectric intermediate layer (4) interposed between the lower electrode (5) and the crystalline zinc oxide-containing dielectric layer (2), the intermediate layer (4) having an intermediate layer thickness (41) of 20 nm to 500 nm.

2. The capacitor structure as claimed in claim 1, with the intermediate layer (4) at least comprising at least one ceramic material selected from the group consisting of aluminum oxide, silicon dioxide, titanium dioxide and zirconium dioxide.

3. The capacitor structure as claimed in claim 1, with the crystalline zinc oxide-containing dielectric layer (2) having a layer thickness (21) of 0.1 μm to 20 μm.

4. The capacitor structure as claimed in claim 1, with the lower electrode layer (5) comprising an electrode material selected from the group consisting of tungsten and platinum.

5. The capacitor structure as claimed in claim 1, with the upper electrode layer (6) comprising an electrode material selected from the group consisting of aluminum and gold.

6. The capacitor structure as claimed in claim 1, with the substrate (3) being a semiconductor substrate with a semiconductor material.

7. A method for producing the capacitor structure as claimed in claim 1 having the method steps:
    a) providing the substrate (3)
    b) producing the lower electrode layer (5) on a substrate surface (31) of the substrate (3)
    c) producing the amorphous intermediate layer (4) on the lower electrode layer (5)
    d) producing the crystalline zinc oxide-containing dielectric layer (2) on the intermediate layer (4), and
    e) producing the upper electrode layer (6) on the crystalline zinc oxide-containing dielectric layer (4).

8. The method as claimed in claim 7, with a deposition being carried out from a vapor phase in order to produce the lower electrode layer (5), the amorphous intermediate layer (4), the crystalline zinc oxide-containing dielectric layer and/or the upper electrode layer (6).

9. The method as claimed in claim 8, with a deposition of zinc oxide from the vapor phase being carried out in order to produce the crystalline dielectric layer (2) and an electrical field being generated during the deposition of the zinc oxide, said electrical field being tipped in respect of a normal of the surface of the lower electrode layer (5).

10. Method of using the capacitor structure as claimed in claim 1 as a piezo-acoustic resonator, with the crystalline zinc oxide-containing dielectric layer forming a piezo-electric layer of the resonator (10) and the piezo-electric layer (2) and the electrode layers (5, 6) being arranged next to one another such that an electrical control of the electrode layers (5, 6) results in the resonator (10) vibrating at a specific resonance frequency.

11. The method as claimed in claim 10, with the resonance frequency of the vibration being selected from the range of exclusively 500 MHz to exclusively 10 GHz.

12. The method as claimed in claim 10 for detecting at least one substance of a fluid (13), with the following method steps being carried out:
    a) combining the fluid (13) and the piezo-acoustic resonator (10) such that the substance is able to be sorbed on the surface segment (12) of the resonator (10) and
    b) determining a resonance frequency of the resonator (10), with the substance being concluded from the resonance frequency on the quantity sorbed by the surface segment (12).

13. The method as claimed in claim 12, with a surface segment (12) for sorbing a substance of a fluid (13) being arranged at the resonator (10) such that the resonance frequency of the resonator (10) is dependent on a quantity of the substance sorbed at the surface segment (12).

14. The method as claimed in claim 12, with the surface segment (12) being formed to sorb the substance of the fluid (13) from a chemically sensitive coating (14) of the resonator (10).

15. The method as claimed in claim 12, with the resonance frequency being determined in the presence of the fluid (13).

16. The capacitor structure as claimed in claim 1, with the intermediate layer thickness being from 50 nm to 200 nm.

17. The capacitor structure as claimed in claim 1, with the intermediate layer thickness being sufficient to achieve a tipping of zinc oxide monocrystals.

18. A capacitor structure (1) for forming a piezo-acoustic resonator, comprising:
   a lower electrode layer (5) arranged on a substrate surface (31) of a substrate (3);
   an upper electrode layer (6);
   a crystalline zinc oxide-containing dielectric layer (2) arranged between the electrode layer (5, 6), the zinc oxide-containing dielectric layer (2) having a plurality of zinc oxide monocrystals each with a polar crystal axis, the polar crystal axes of the zinc oxide monocrystals of the dielectric layer being tipped relative to the substrate surface (31); and
   an amorphous dielectric intermediate layer (4) interposed between the lower electrode (5) and the crystalline zinc oxide-containing dielectric layer (2), the intermediate layer (4) having an intermediate layer thickness (41) of 20 nm to 500 nm, the with the intermediate layer thickness being sufficient to achieve a tipping of the zinc oxide monocrystals.

19. The capacitor structure as claimed in claim 18, with the zinc oxide monocrystals having a tipping of a c-axis of the monocrystals at approximately 16° toward a normal of the substrate's surface.

* * * * *